United States Patent
Blankertz et al.

(10) Patent No.: US 6,331,656 B1
(45) Date of Patent: Dec. 18, 2001

(54) HYDROFORMYLATION PROCESS

(75) Inventors: Heinrich-Josef Blankertz, Forst; Armin Volker Grenacher, Mutterstadt; Friedrich Sauer, Obersülzen; Harald Schwahn, Wiesloch; Willi Schönmann, Limburgerhof; Michael Röper, Wachenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/269,421
(22) PCT Filed: Sep. 19, 1997
(86) PCT No.: PCT/EP97/04907
  § 371 Date: Mar. 4, 1999
  § 102(e) Date: Mar. 4, 1999
(87) PCT Pub. No.: WO98/12235
  PCT Pub. Date: Mar. 26, 1998

(30) Foreign Application Priority Data

Sep. 20, 1996 (DE) .............................. 196 38 796

(51) Int. Cl.$^7$ .................................................. C07C 45/00
(52) U.S. Cl. .................. 568/451; 568/909; 585/531; 560/232
(58) Field of Search .................. 568/451, 909; 585/531; 560/232

(56) References Cited

U.S. PATENT DOCUMENTS

| | | | |
|---|---|---|---|
| 2,815,390 | 12/1957 | Gwynn et al. | 260/638 |
| 3,684,735 | 8/1972 | Oppenlaender et al. | 252/342 |
| 3,907,701 | 9/1975 | Liebold et al. | 252/344 |
| 3,932,523 | 1/1976 | Strohmeyer et al. | 240/604 |
| 3,993,615 | 11/1976 | Markofsky et al. | 260/29.2 |
| 4,255,279 | 3/1981 | Sppohn et al. | 252/413 |
| 4,402,820 | 9/1983 | Meis et al. | 252/420 |
| 4,625,067 | * 11/1986 | Nanin | 568/451 |
| 5,286,823 | 2/1994 | Rath | 526/237 |
| 5,661,220 | 8/1997 | Faul et al. | 525/384 |
| 5,832,702 | 5/1989 | Kummer et al. | 44/62 |

FOREIGN PATENT DOCUMENTS

| | | |
|---|---|---|
| 1545250 | 9/1966 | (DE) . |
| 2013820 | 10/1971 | (DE) . |
| 2227546 | 1/1974 | (DE) . |
| 2404855 | 8/1975 | (DE) . |
| 3026900 | 2/1981 | (DE) . |
| 3014044 | 10/1981 | (DE) . |
| 4326772 | 2/1995 | (DE) . |
| 4404742 | 8/1995 | (DE) . |
| 46564 | 3/1982 | (EP) . |
| 244616 | 11/1986 | (EP) . |
| WO 90/05711 | * 5/1990 | (WO) . |

OTHER PUBLICATIONS

Ullmanns Encyk. der Techn. Chemie, vol. 7, 4th Ed. (1974), pp. 120–125.

Falbe, "New syntheses with Carbon Monoxide", pp. 162–165, Springer–Verlag, Berlin (1980).

"Design criteria for electostatic de–emulsifiers", by Josef Draxler and Rolf Marr (Abstract translated into English), Chem. Ing–Tech. 62, (1990–pp. 525–530. (Complete translation not available).

* cited by examiner

Primary Examiner—Paul J. Killos
Assistant Examiner—Taylor Victor Oh
(74) Attorney, Agent, or Firm—John H. Shurtleff

(57) ABSTRACT

In a process for the hydroformylation of olefins having from 12 to 100 carbon atoms in the presence of a cobalt carbonyl catalyst at pressures of from 100 to 400 bar and at from 100 to 200° C., depressurization and recovery of the cobalt catalyst by extraction with an aqueous acid solution in the presence of atmospheric oxygen, (a) the extraction is carried out in the presence of a polymeric emulsion breaker selected from the group consisting of alkoxylated compounds containing amino, imino or OH groups, and (b) to achieve complete phase separation in the organic phase still containing small amounts of aqueous phase, the formation of relatively large droplets of the dispersed aqueous phase is effected in a coalescence stage.

11 Claims, 1 Drawing Sheet

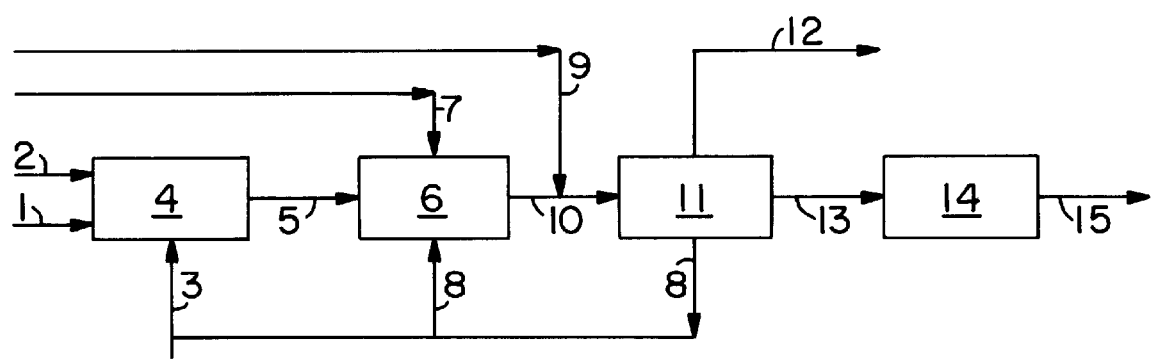

HYDROFORMYLATION PROCESS

The present invention relates to a process for the hydroformylation of olefins having from 12 to 100 carbon atoms at pressures of from 100 to 400 bar and at from 100 to 200° C. using a cobalt catalyst and separation of the catalyst, with the extraction of the catalyst being carried out in the presence of an emulsion breaker and using a downstream coalescence stage.

The hydroformylation of olefins using a cobalt catalyst at from 100 to 200° C. and pressures of from 100 to 400 bar is a well-tried process in industry (Ullmanns Enzyklopädie der Technischen Chemie, Volume 7, Pages 120ff).

In such a process, the cobalt catalyst is generally used in the form of the acetate or formate or else in the form of soluble salts of higher carboxylic acids, eg. as cobalt ethylhexanoate. Preferably, cobalt formate or cobalt acetate is fed in as an aqueous solution in amounts of from 0.1 to 3 percent by weight, based on the olefin to be hydroformylated. Further details may be found in the monograph by J. Falbe, New Syntheses with Carbon Monoxide, Springer Verlag, 1970, 162–165.

For reasons of economics and to free the hydroformylation product of catalyst, the cobalt which is present in the form of cobalt carbonyl or cobalt hydridocarbonyl has to be separated off as completely as possible and returned to the synthesis stage.

This is usually achieved, according to DE-A 24 04 855, U.S. Pat. No. 2,404,855 by treating the oxo reaction mixture with molecular oxygen in the presence of aqueous acid. The cobalt is thus oxidized from the oxidation state –1 to +2 and can then be removed by extraction with the aqueous solution. The aqueous extract is separated off, for example, by decantation, in a phase-separation vessel or in other apparatuses suitable for this purpose.

Other methods (see Ullmanns Enzyklopädie der Technischen Chemie, Vol. 7, p. 123) employ the thermal decomposition of the cobalt carbonyls for separating them from the reaction mixture. For this purpose, the CO partial pressure is lowered by depressurizing the reaction product and superheating steam is introduced. The precipitated cobalt hydroxide, oxide or metal is then separated off mechanically or by dissolving in $HNO_3$.

In another embodiment, the reaction product containing the cobalt hydridocarbonyl is scrubbed using an aqueous sodium carbonate solution which takes up the acid hydridocarbonyl. The catalyst can be set free again from the aqueous phase using, for example, sulfuric acid and can be recirculated.

It is also possible to combine various cobalt removal methods. Thus, DE-A 30 26 900 U.S. Pat. No. 3,932,523 proposes, in a first step, extracting the cobalt hydridocarbonyl from the organic phase in the form of the complex salt $Co(CO(CO)_4)_2$ using an aqueous cobalt(II) salt solution and, in a second step, removing residues of the cobalt catalyst by treatment with air and acid.

The reaction product which has been freed of cobalt can then be processed further in a customary manner, eg. by distillation, hydrogenation or hydrogenative amination.

While short-chain olefins are now hydroformylated predominantly at relatively low pressures in the presence of rhodium catalysts, the hydroformylation of higher olefins having 12 and more carbon atoms using cobalt catalysts has retained its importance.

An application of the hydroformylation reaction using a cobalt catalyst which is of particular interest is, according to EP-A 244 616, the hydroformylation of polybutenes or polyisobutenes to give polybutyl- or polyisobutylaldehydes, alcohols or esters.

A subsequent hydrogenated amination of the oxo product gives polybutylamines or polyisobutylamines, which are valued components for the formulation of lubricants and fuel additives.

However, owing to the high viscosity and the surface-active properties of the oxo products of the polyisobutenes, an effective removal of the cobalt catalyst used can be achieved only with difficulty. Polyisobutene oxo products tend to form an intimate bond with the cobalt carbonyl from which the catalyst is extremely difficult to isolate. Although thermal cobalt removal would effectively destroy the carbonyls, separating off the cobalt hydroxide by, for example, filtration is hard to imagine because of the high viscosity.

Likewise, cobalt removal methods based on extraction of the cobalt hydridocarbonyl, either with oxidation of the cobalt from –1 to +2 or with retention of the oxidation state, have their limitations. Here, the tendency of the polyisobutene oxo products to form stable emulsions with aqueous phases is a noticeable disadvantage.

Since the hydroformylation reaction using a cobalt catalyst is carried out at elevated pressures of from 100 to 400 bar, it is necessary in all process variants to depressurize the crude product to pressures of customarily less than 50 bar for further work-up.

This often results, particularly in the case of a multiphase depressurization with an aqueous solution being introduced for the cobalt extraction, in strong shear fields which favor the formation of emulsions. The high energy input during dispersion causes the formation of very small droplets; a fine dispersion or emulsion is formed.

If water-in-oil emulsions are present owing to the phase ratio between aqueous and organic phases, these are additionally stabilized by the high viscosity ratio between aqueous and organic phases. Depending on the operative conditions, these emulsions of aqueous and organic phases can be stable for a number of days. As a result, the circulation of the aqueous phase is as impossible as the further processing of the hydroformylated polyisobutene.

However, to carry out the hydroformylation economically it is necessary to achieve complete separation and recirculation of the cobalt catalyst used after passage through the reaction stage, since this, on the one hand, lowers the costs for the process and on the other hand the further processing in the subsequent process stages is made significantly easier.

It is an object of the present invention to carry out the hydroformylation in such a way that the cobalt catalyst used can be virtually completely separated off and substantially circulated, and an oxo product suitable for further processing, ie. largely free of cobalt, is obtained.

We have found that this object is achieved by a process for the hydroformylation of olefins having from 12 to 100 carbon atoms in the presence of a cobalt carbonyl catalyst at pressures of from 100 to 400 bar and at from 100 to 200° C., depressurization and recovery of the cobalt catalyst by extraction with an aqueous acid solution in the presence of atmospheric oxygen, wherein (a) the extraction is carried out in the presence of a polymeric emulsion breaker selected from the group consisting of alkoxylated compounds containing amino, imino or OH groups, and (b) to achieve complete phase separation in the organic phase still containing small amounts of aqueous phase, the formation of relatively large droplets of the dispersed aqueous phase is effected in a coalescence stage, preferably with the aid of a packed column.

Suitable emulsion breakers are alkoxylated compounds as are customarily used in the petroleum industry for removing the salt-containing water. These are, for example, (a) oligo- and polyamines and -imines alkoxylated with propylene oxide and possibly ethylene oxide in addition and also (b) alkoxylated alkylphenol-formaldehyde resins and (c) ethylene oxide/propylene oxide block polymers and also (d) their polymeric acrylic esters as are described in DE-A 22 27 546 and DE-A 24 35 713 (a); DE-A 20 13 820 (b); DE-A 15 45 250 (c); and DE-A 43 26 772 (d).

Particular preference is given to using an emulsion breaker which is obtained by reacting polyethylenimine having a MW of from 10,000 to 50,000 with propylene oxide and optionally ethylene oxide in amounts such that the content of alkoxy units is from 90 to 99% by weight.

The amount of demulsifier which is added to achieve the desired effect is from about 0.1 to 100 g per metric t of the organic material used, preferably from 2 to 20 g/metric t.

The demulsifier is preferably added continuously in dilute form. Dilution with an inert solvent, eg. o-xylene, aids handling and metering in of the small amount needed. It is advantageously added after cobalt removal, preferably combined with the addition of the aqueous extraction solution and the air on depressurization, which effectively mixes in the demulsifier.

The pretreated dispersion comprising aqueous and organic phases can subsequently be separated in a calming zone. This is advantageously achieved in a horizontal, continuously operated phase-separation vessel through which there is a low flow velocity. As a result of the different densities of the phases, the dispersion separates under gravity so that both phases are present in closed form and largely free of foreign phases as layers above one another. The aqueous phase obtained is completely free of organic phase so that the cobalt salt solution can be returned without further work-up to the cobalt removal stage.

The organic phase generally still contains from 1 to 5% by weight of foreign phase-, preferably in the form of very fine droplets. Although the water content itself does not interfere with further processing, the cobalt salts and acids dissolved therein are undesirable in the subsequent reactions.

The residual water can then be separated off by passing the very fine dispersion through a bed of packing, preferably from the top downward. Wetting of the large surface area of the packing results in surface coalescence and at the same time in droplet-droplet coalescence by means of droplet motion. Preference is given to using packed columns which are filled with metal rings. The large droplets of the aqueous phase which form quickly separate out and can be taken off as a lower phase. The oxo product is taken off above the phase separation layer and, under usual conditions, then still contains from 0.05 to 0.3% by weight of suspended water.

The separation of the finely dispersed residual water from the organic phase by coalescence of the water droplets to form larger droplets can also be carried out with the aid of other equipment, for example by means of electrostatic coalescence apparatuses as are described, for example, in Chem. Ing. Techn. 62, (1990) 525. However the coalescence of the aqueous phase of the fine dispersion by passing it through a bed of packing, in particular through a packed column, proves to be particularly advantageous and economical for achieving the object of the present invention.

The separation of the droplets is aided if the apparatus is operated at elevated temperatures of from 50 to 100°, preferably 80° C. The viscosity of the organic phase is then lower and the velocity at which the droplets sink is correspondingly increased. The separation of the droplets can also be carried out at lower temperatures, for example at room temperature, at which the rate of separation of the droplets is slowed down as a function of the viscosity of the organic phase.

To remove remaining amounts of entrained dispersed cobalt-containing aqueous phase it is advantageous to install a downstream phase-separation apparatus with commercial coalescence filter candles in which the aqueous phase is separated out to values corresponding to the solubility, so that the cobalt content in the oxo product is reduced to values below 10 ppm of Co for a polyisobutene oxo product or below the detection limit for a $C_{13}$–$C_{21}$ oxo product.

The aqueous phases separated off in the above steps are advantageously combined and returned to cobalt removal. The amount of aqueous cobalt salt solution required for feeding the reactor can be diverted from this circuit without any special measures.

In particular, any traces of the emulsion breaker still present can remain in the cobalt salt solution without resulting in undesired by-product formation in the hydroformylation reaction.

Suitable olefins to be hydroformylated are, on the one hand, polybutenes and in particular polyisobutenes having from 28 to 100 carbon atoms. Particularly preferred polyisobutenes are those having terminal double bonds, as are described, for example, in U.S. Pat. No. 5,286,823.

Furthermore, the process of the present invention is suitable for hydroformylating $C_{12}$–$C_{20}$ olefins in order to prepare detergent alcohols.

An advantageous embodiment of the process is explained in detail with the aid of the schematic FIGURE:

Olefin and synthesis gas (oxo gas) and also an aqueous cobalt salt solution 3 are fed to the hydroformylation reactor via lines 1 to 3. In reactor 4, the reaction with oxo gas to give the oxygen-containing compounds takes place under customary hydroformylation conditions. The reaction product containing the active catalyst in the form of the cobalt hydridocarbonyl is fed via line 5 to cobalt removal 6 and is there treated with air via line 7 and an aqueous acid cobalt salt solution. In this step, the cobalt changes its oxidation state from −1 to +2 and is dissolved in the acid aqueous phase as cobalt salt. Immediately after cobalt removal, ie. virtually in the same stage, the demulsifier is added via line 9 and the crude reaction product is conveyed via line 10 to a phase-separation vessel 11. Here, the gas phase and the two liquid phases separate. The unreacted air and also the CO and $H_2$ carried over from the synthesis stage are discharged via line 12. The aqueous phase 8 which separates out is partly returned to the cobalt removal stage 6 and partly to the hydroformylation 4.

The cobalt salt solution used for the oxo reaction and for the extraction is preferably a cobalt formate or cobalt acetate solution which has been adjusted to a pH of about 2–5, but preferably 3–4, using formic acid or acetic acid. The concentration of $Co^{+2}$ in the solution is from 0.5 to 2% by weight, advantageously from 1.0 to 1.5% by weight.

The reaction of the olefin in the synthesis reactor is carried out at from 100 to 400 bar, preferably from 250 to 300 bar, and at from 100 to 200° C., preferably from 150 to 190° C.

To remove the cobalt hydridocarbonyl, the oxo product is treated with molecular oxygen via line 7 in the presence of the aqueous acid cobalt solution from line 8. In general, the weight of aqueous phase used is from 0.1 to 10 times, particularly advantageously from 0.5 to 0.9 times, that of the organic phase.

The molecular oxygen is advantageously introduced in the form of air whose amount is calculated such that the number of moles of oxygen present is from 2 to 2.5 times the number of gram atoms of cobalt.

The mixing of the liquid phases and the oxygen-containing gas phase can be carried out in any apparatus for carrying out gas/liquid reactions, eg. in a bubble column, an intensively stirred mixing vessel or a two-fluid nozzle.

In a preferred embodiment, the mixture of the three phases after passing through the cobalt removal zone can be conveyed through a dispersion apparatus. Mixing elements suitable for this purpose are customary static mixers and also packing elements (eg. Raschig rings, Pall rings, glass spheres, etc). This gives intimate mixing as well as a narrow droplet size distribution of the dispersed aqueous phase which aids the subsequent phase separation.

After the phase separation 11, the organic phase containing small amounts of the aqueous phase is conveyed via line 13 to a coalescence stage 14, preferably a packed column which is filled with metal packing elements, eg. metal rings.

The liquid generally flows through the packed column from the top downward and empty-tube velocities of from 0.1 to 1.0 cm/sec and residence times of from 10 to 60 minutes are advantageously employed. The choice of shape and material of the packing elements is free; however, they should be able to be wetted by the liquid phase. This is generally the case for metal packing elements, eg. rings of stainless steel.

Downstream of the coalescence stage there is located a further phase-separation vessel (not shown in the figure) in which the droplets of aqueous phase which have been enlarged in the coalescence stage are separated out, giving a product 15 which is virtually free of aqueous phase and can be worked up in a customary manner.

The process of the present invention is illustrated by the following examples.

EXAMPLES

Example 1
(Comparison; not according to the present invention)

3 660 kg/h of a mixture of 1 940 kg/h of polyisobutenes and 1 720 kg/h of a $C_{12-14}$-paraffin hydrocarbon fraction were fed into a hydroformylation reactor. At the same time, 300 kg [sic] of an aqueous, acid cobalt formate solution whose pH had been adjusted to about 3.4 with formic acid and which contained 1.3% by weight of cobalt were fed to the reactor. In the reactor, the formation of the active catalyst and a hydroformylation reaction took place at from 180 to 185° C. To maintain a total pressure of about 270 bar, a gas mixture comprising 40% by volume of CO and 59% by volume of $H_2$ (+1% of inerts) was fed to the reactor so that the pressure remained constant.

After passing through the reaction section, the product was depressurized in a cobalt removal stage in which the pressure was lowered from 270 to about 20 bar. In addition, 2 600 kg/h of cobalt salt solution having the abovementioned composition and 17 kg/h of air were fed into the cobalt removal stage.

After the cobalt removal stage, 200 kg/h of depressurization gas were separated off in a phase separator and conveyed to a collection system.

The remaining liquid phases were separated from one another. The aqueous phase was largely free of organic material, but contained, apart from $Co^{+2}$, about 0.3% by weight of cobalt carbonyls.

The organic phase still contained about 1.6% by weight of foreign phase and the cobalt content was 200 ppm. The polyisobutylene used had been reacted to an extent of 93%. 62% of the polyisobutene reacted had been converted into the desired products polyisobutyl aldehyde, alcohol or ester.

Example 2
(according to the present invention)

3 660 kg/h of a mixture of 1 940 kg/h of polyisobutenes and 1 720 kg/h of a $C_{12-14}$-paraffin hydrocarbon fraction were fed into a hydroformylation reactor. At the same time, 300 kg/hr of an aqueous, acid cobalt formate solution whose pH had been adjusted to about 3.4 with formic acid and which contained 1.30% by weight of cobalt were fed to the reactor.

In the reactor, the hydroformylation reaction took place at from 180 to 185° C. The reactor pressure of about 270 bar was kept constant by feeding in the necessary amount of oxo gas.

After passing through the reaction section, the product was depressurized in a cobalt removal stage in which the pressure was lowered from about 270 to 20 bar. In addition, 2 600 kg/h of cobalt salt solution having the abovementioned composition and 17 kg/h of air were fed into the cobalt removal zone. Immediately after the product left the metal removal stage, an emulsion breaker was added as dilute solution in such an amount that the concentration of breaker was 12 g per metric t of reaction product. The emulsion breaker was a polyethylenimine modified with propylene oxide (molecular weight of the polyethylenimine used for the preparation: about 20 000; content of propoxy units: 99% by weight).

The combined streams from the cobalt removal stage were passed through a tube section filled with packing elements; the residence time in the section was about 1 minute. The packed section had dimensions such that a differential pressure of 3.6 bar was established.

After the mixing section, 200 kg/h of depressurization gas were separated off in a calming zone and conveyed to a collection system.

The liquid phases were separated from one another. The aqueous phase was largely free of organic material and the cobalt carbonyl content was only 0.05% by weight.

The organic phase still contained about 0.7% by weight of foreign phase. Conversion and yield corresponded to the values in Example 1.

To remove the remaining amount of cobalt salt solution, the reaction product was cooled to 80° C. and passed through a bed of packing having a length of 6.5 m and a diameter of 70 cm. The empty-tube velocity in this section was about 0.3 cm/s. The section was arranged vertically and the liquid flowed through it from the top downward. The aqueous solution which separated out collected in the lower part of the apparatus and was taken off there. The organic phase was taken off above the phase boundary and still contained 0.14% by weight of water The cobalt content of the organic phase was below 10 ppm.

Example 3

When the emulsion breaker used was a compound which had been prepared by alkoxylation of trimethylolpropane with 60 mol of propylene oxide and 10 mol of ethylene oxide and esterification of the resulting polyol with acrylic acid, similar results with a cobalt content of less than 10 ppm were obtained.

We claim:
1. A process for the hydroformylation of olefins having from 12 to 100 carbon atoms in the presence of a cobalt carbonyl catalyst at pressures of from 100 to 400 bar and at from 100 to 200° C., depressurization and recovery of the cobalt catalyst by extraction with an aqueous acid solution in the presence of atmospheric oxygen, wherein
  (a) the extraction is carried out in the presence of a polymeric emulsion breaker selected from the group consisting of alkoxylated compounds containing amino, imino or OH groups, and
  (b) to achieve complete phase separation in the organic phase still containing small amounts of aqueous phase, the formation of relatively large droplets of the dispersed aqueous phase is effected in a coalescence stage.

2. A process as claimed in claim 1, wherein the emulsion breaker used is a polyethyleneimine alkoxylated with propylene oxide and/or ethylene oxide.

3. A process as claimed in claim 1, wherein the coalescence stage comprises a packed column with a downstream phase-separation apparatus.

4. A process as claimed in claim 1, wherein a vertical packed column is used in the coalescence stage (b), with the packing elements comprising a material which is wetted by the dispersed aqueous phase and the bed of packing being flooded by the organic phase.

5. A process as claimed in claim 1, wherein a packed column filled with metal rings is used in the coalescence stage (b).

6. A process as claimed in claim 1, wherein the emulsion breaker is used in concentrations of from 0.1 to 100 ppm in the extraction mixture.

7. A process as claimed in claim 1, wherein a temperature of from 50 to 120° C. is maintained in the coalescence stage.

8. A process as claimed in claim 1, wherein the separation of the large droplets of aqueous cobalt-containing phase formed in stage (b) and the organic phase is carried out by means of a phase-separation vessel below the bed of packing.

9. A process as claimed in claim 1, wherein polyisobutene having from 28 to 100 carbon atoms is hydroformylated.

10. A process as claimed in claim 1, wherein olefins having from 12 to 20 carbon atoms are hydroformylated.

11. A process as claimed in claim 1, wherein the coalescence stage (b) is carried out by means of an electrostatic coalescence apparatus.

* * * * *